(12) United States Patent
Huang et al.

(10) Patent No.: US 7,071,227 B2
(45) Date of Patent: Jul. 4, 2006

(54) ANTIVIRAL COMPOSITIONS AND METHODS OF USE

(75) Inventors: Ru Chih C. Huang, Baltimore, MD (US); Ibrahim Shawky Abd Elazem, Baltimore, MD (US); Hong Shan Chen, Beijing (CN)

(73) Assignee: The Johns Hopkins University, Baltimore, MD (US)

( * ) Notice: Subject to any disclaimer, the term of this patent is extended or adjusted under 35 U.S.C. 154(b) by 600 days.

(21) Appl. No.: 09/962,923

(22) Filed: Sep. 25, 2001

(65) Prior Publication Data

US 2002/0151584 A1 Oct. 17, 2002

Related U.S. Application Data

(60) Provisional application No. 60/235,425, filed on Sep. 26, 2000.

(51) Int. Cl.
*A01N 43/08* (2006.01)
*C07D 307/87* (2006.01)

(52) U.S. Cl. ................. 514/469; 514/885; 549/469
(58) Field of Classification Search ............... 514/469, 514/769, 885; 549/436
See application file for complete search history.

(56) References Cited

OTHER PUBLICATIONS

Lim et al , Phytoherapy Research 11(7) , "Inhibitory effects of Cordia spinescens extracts and their constituents on reverse transcriptase and protease from human immunodeficency", pp. 490-495 (1997).*
Lim et al, Chem. Abs. vol. 128 No. 43466 (1997).*
Ebersold et al "Human and nurine monoclonal antibody . . . " CA 117:169322 (1992).*
Scarlatti et al "In vivo evolution . . . " CA.*
Cho et al "Identification of determinants . . . " CA 128:216242 (19998).*
Howard et al "Inhibition of in vitro and in vivo . . . " CA 129:49262 (1998).*
Richman "Antiretroviral drug . . . " Activiral chemotheraphy 4 ed. Mills, Plenum Press, p. 383-395 (1996).*
Yarchoan et al "Challenges in the therapy of HIV infection" Clinical perspective TIPS p. 196-202 (19993).*
Flexner et al "Pharmacology of antiretrviral agents" AIDS:biology, daig,Treat. Vincent ed. Lippicott, p. 479-493 (1997).*

* cited by examiner

*Primary Examiner*—Cecilia J. Tsang
*Assistant Examiner*—Raymond Covington
(74) *Attorney, Agent, or Firm*—Whitham, Curtis, Christofferson & Cook PC

(57) ABSTRACT

Purified antiviral compounds, pharmaceutical formulations containing the compounds, and methods of use of the compounds are provided. The compositions of the invention are isolated antiviral components from plant extracts derived from, for example, *Salvia miltiorrhiza*, that find use in the treatment of viral infections, such as by inhibiting the activity of viral integrase. Methods for isolation and purification of the antiviral compounds are additionally provided.

11 Claims, 9 Drawing Sheets

ANTIVIRAL COMPOSITIONS AND METHODS OF USE

CROSS-REFERENCE TO RELATED APPLICATIONS

This application claims the benefit of U.S. Provisional Application No. 60/235,425, filed Sep. 26, 2000, which is incorporated by reference herein in its entirety.

FEDERALLY SPONSORED RESEARCH OR DEVELOPMENT

The invention received funding from the National Institutes of Health under Grant No. 3ROIDE12165.

FIELD OF THE INVENTION

The present invention relates to compositions and methods for the prevention and treatment of viral infections, particularly retroviral infections.

BACKGROUND OF THE INVENTION

Viruses consist of either double-stranded or single-stranded DNA or RNA enclosed in a protein coat, called a capsid. Some viruses also possess a lipoprotein envelope that, like the capsid, may contain antigenic proteins. Since viruses have no metabolic machinery of their own, they usurp the machinery of their host cell which, depending on the virus, may be a plant, bacterium, or animal cell.

A viral infection begins when a virion comes into contact with a host cell and attaches, or adsorbs, to it. The viral DNA or RNA then crosses the plasma membrane into the cytoplasm and eventually enter into the nucleus. In the case of retrovirus, the viral RNA is reverse transcribed into DNA. Viral DNA is then integrated into the chromosomal DNA of the infected cell. Integration is mediated by an integration protein, integrase. All integrated proviruses are required for the subsequent transcription process which is acted upon by the host cell transcription factors. The integrated DNA is transcribed by the cell's own machinery into mRNA, or replicated and becomes enclosed in a virion. For retrovirus, the integrated DNA is transcribed into RNA that either acts as mRNA or become enclosed in a virion. This completes the virus life cycle.

In the past decade, the emergence of human immunodeficiency virus type 1 (HIV-1) as an important human pathogen has led to a resurgence of scientific interest in retroviruses. HIV-1 is the primary etiologic agent of AIDS, a fatal disease that results from the gradual destruction of the helper T-cell population in infected individuals. The importance of HIV-1 as a human pathogen has led to its being the major focus of research into lentivirus replication and gene regulation. Indeed, HIV-1 may be viewed as the prototype of not only the lentivirus subgroup but also, more broadly, complex retroviruses in general.

There are an estimated 650,000 to 900,000 people currently living with HIV in the United States, with approximately 40,000 new HIV infections occurring here every year. As of June 1999, 711,344 AIDS cases have been reported in the United States. Since the beginning of the epidemic, 420,201 AIDS deaths have been reported. The scale of the AIDS epidemic demands the development of efficient and affordable AIDS therapeutics.

While HIV-1 relies heavily on the cellular host enzymes for many of the steps required in its replication, the virus carries in its genome the genetic information that leads to the synthesis of its unique retroviral enzymes, such as the three enzymes encoded by its pol gene: reverse transcriptase, proteases, and integrase. Effective antiviral agents must inhibit virus-specific replicative events or preferentially inhibit virus-directed rather than host cell-directed nucleic acid or protein synthesis. To date, of the numerous compounds that have already been identified and approved for marketing by the FDA for HIV, only drugs inhibiting the activities of reverse transcriptase and protease inhibitors have been identified. The first drug to be introduced was suramin, a reverse transcriptase inhibitor. Subsequently, AZT and other compounds (zalciabine (ddC), didanosine (ddI), compound Q, ritonavir, etc.) have also been found to possess anti-HIV activity in vitro. Specifically, AZT was approved by the FDA in 1987.

Even though the current therapeutic agents are effective in inhibiting the enzymatic activity which is essential for the viral life cycle, the small fraction of remaining viruses unfortunately mutate and continue to replicate even in the presence of these drugs. High rates of replication, viral sequence mutation, and rapid turnover of the viral population are typical traits of retroviruses. These traits are even more striking in the case of HIV-1. As result, these drugs show little long term benefits in terms of a complete treatment or prevention of HIV-infection. Recent studies have demonstrated that combinatorial therapy against reverse transcriptase (RT) and protease can eliminate a majority of the HIV viruses in T lymphocytes. There is, therefore, need for additional therapeutic agents to be added to the treatment cocktail for viral infections, particularly retroviral infections.

The viral integrase catalyses the integration of the viral DNA into the host DNA, which is an essential step in the viral life cycle. There is no know human homologue to this enzyme and therefore potential inhibitors could be both efficacious and non-toxic. However, drugs targeting integrase have been slow to emerge because of the lack of structural information on this poorly soluble protein. Current search on integrase inhibitor has relied more on empirical testing than on drug design.

*Salvia miltiorrhiza* is a traditional Chinese medicinal herb for treatment of cardiovascular and hepatic diseases. Extracts from *S. miltiorrhiza* and its related species exhibit anti-viral and antioxidant activities that are health beneficial. See Meng et al. (1992) *Chung Kuo Chung Hsi I Chieh Ho Tsa Chih* 12, 345–347, 324–35; Xiong (1993) *Chung Kuo Chung Hsi I Chieh Ho Tsa Chih* 13, 33–35, 516–517; U.S. Pat. No. 5,178,865; U.S. Pat. No. 5,411,733; U.S. Pat. No. 6,043,276; International PCT Application 98/24460; Chinese Patent Application Nos. 1,192,922 and 1,192,918. Antiviral agents active against herpes, polio, measles, varicellazoster, cytomegalovirus, DNA viruses and RNA viruses have been described which contain at least one crude drug from the root of *S. miltiorrhiza* Bunge (See European Patent No. 0 568 001 A2). Seven phenolic compounds isolated from the aqueous extract of *S. miltiorrhiza* demonstrate a strong protective action against peroxidative damage to liver microsomes, hepatocytes, or erythrocytes (See Liu, et al., 1992, *Biochem. Pharmacol.* 43, 147–1952). Lithospermic acid B was identified as an active component in an extract of *Salvia miltiorrhiza radix* that was shown to exhibit endothelium-dependent vasodilation in the aorta and may be useful in the treatment of hypertension (See Kamata, et al., 1993, *Gen. Pharmacol.* 24, 977–981). The therapeutic effect of these extract has been attributed in part to the ability of the plant to accumulate active compounds such as transhinones and phenolic compounds.

Therefore, there remains a need in the art for the identification of additional compounds capable of treating viral infections, particularly compounds that inhibit viral integrase.

SUMMARY OF THE INVENTION

Purified antiviral compounds, pharmaceutical formulations containing the compounds, and methods of use of the compounds are provided. The compositions of the invention are isolated antiviral components from plant extracts that find use in the treatment of viral infections. In particular, it is believed that the compounds of the invention inhibit the activity of viral integrase. The purified compounds are represented by Formula (I):

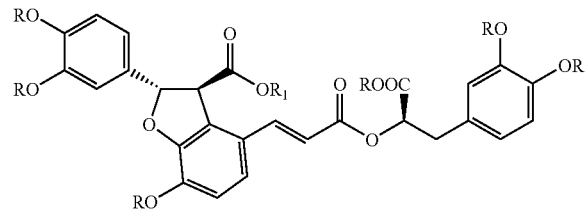

wherein:

each R is independently H or an alkyl group, such as a C1–C4 alkyl; and $R_1$ is H, alkyl, substituted alkyl, aryl or substituted aryl, and pharmaceutically acceptable salts thereof.

Preferably, each R is selected from the group consisting of H and methyl and $R_1$ is an alkyl group substituted with a substituted phenyl group and a carboxyl group. Preferred substituents on the phenyl ring include one or more hydroxyl groups. Preferably, the purified compounds have a purity of at least about 90%, more preferably at least about 95%, and most preferably at least about 99%.

Methods for the isolation of the antiviral compounds are also provided. The isolation method comprises providing plant material, such as *Salvia miltiorrhiza*, and extracting an alcohol-soluble fraction therefrom. The roots of the Salvia plant are particularly preferred. A group of compounds are precipitated from the alcohol-soluble fraction and separated into an aqueous layer and an organic layer. Thereafter, chromatography can be used to isolate at least one compound of Formula (I) from the organic layer. For example, high performance liquid chromatography (HPLC) can be used in the isolation step.

Methods for treatment or prevention of viral infection, or the disease that it causes it, using the compounds of Formula (I) are also provided. The method involves administering to a population of cells, either in vitro or in vivo, a therapeutically effective amount of a purified compound of Formula (I) or a pharmaceutically acceptable salt thereof. The compound of Formula (I) may be administered alone or as part of a pharmaceutical composition comprising the purified compound, one or more pharmaceutically acceptable carriers and, optionally, one or more additional antiviral agents. In specific embodiments, methods are provided to treat and/or prevent HIV-1 infection and to treat and/or prevent AIDS by inhibiting the integrase activity of HIV-1. The compositions of the invention find use in inhibiting viral replication in a mammal, particularly a human being.

BRIEF DESCRIPTION OF THE DRAWINGS

Figures 1A, 1B:
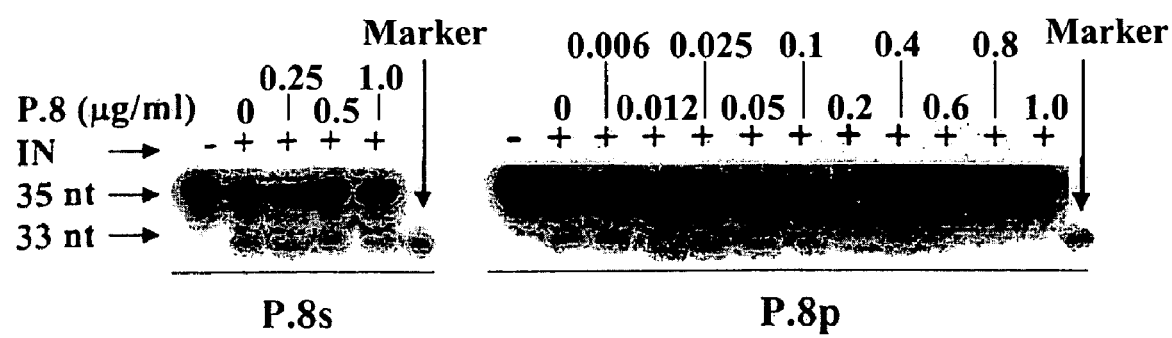
Figure 2A:
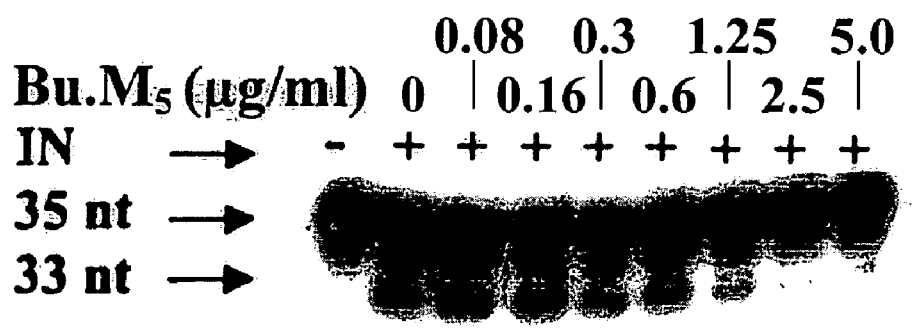
Figure 2B:
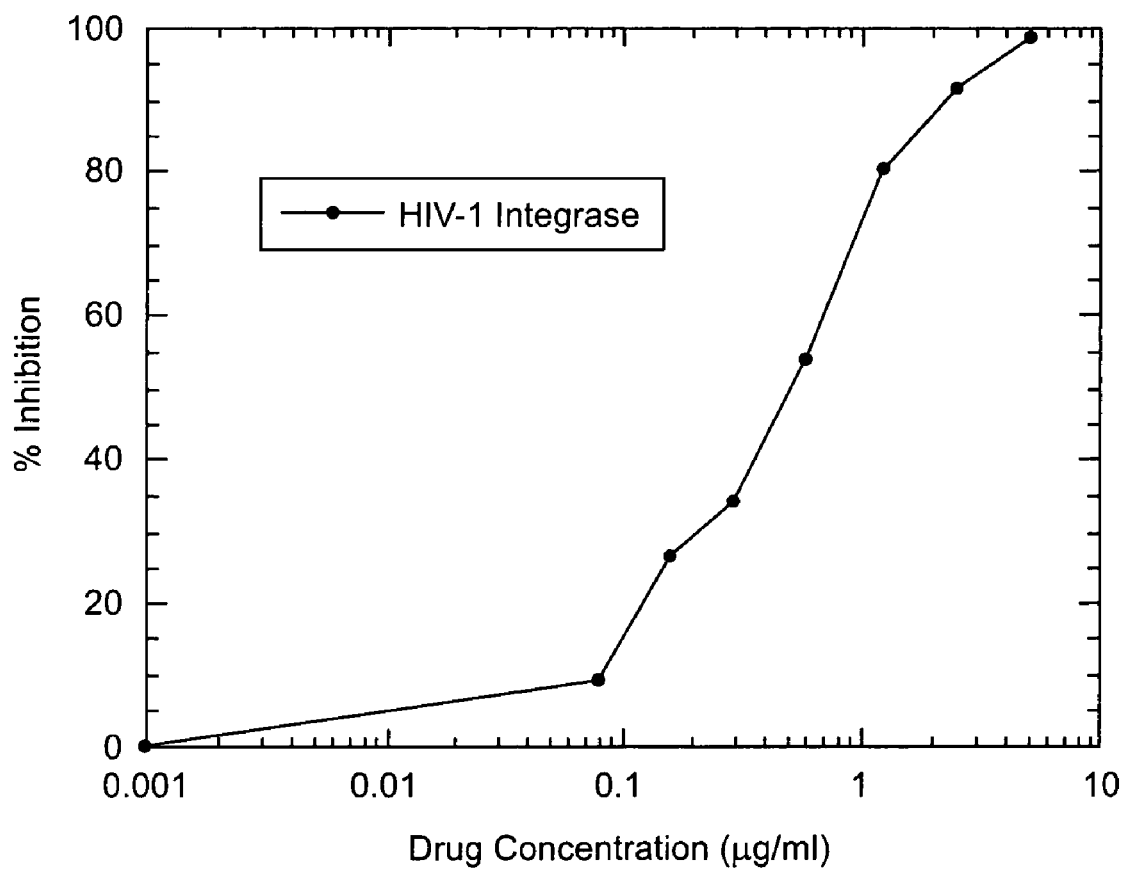
Figure 3:
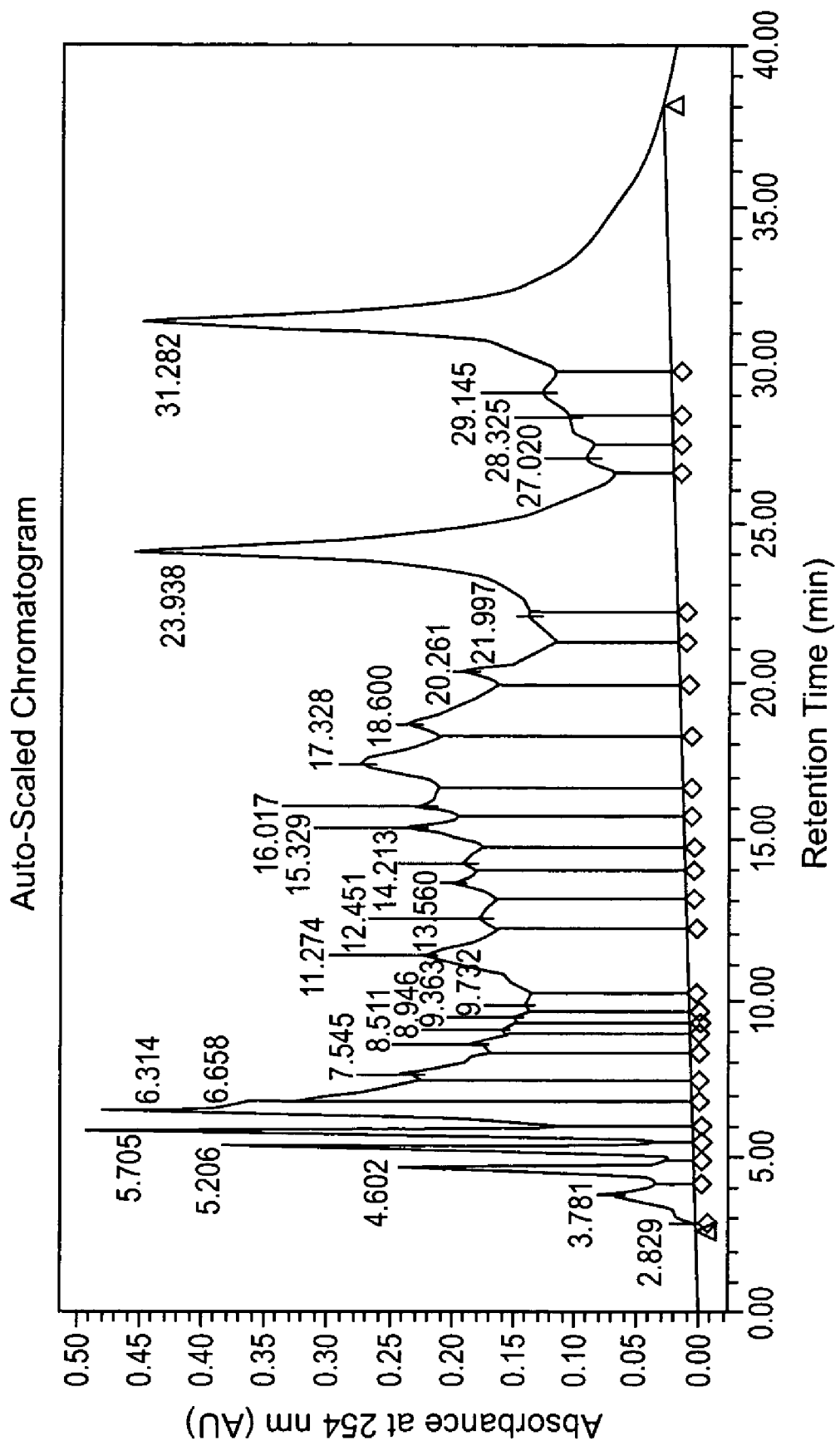
Figure 4A:
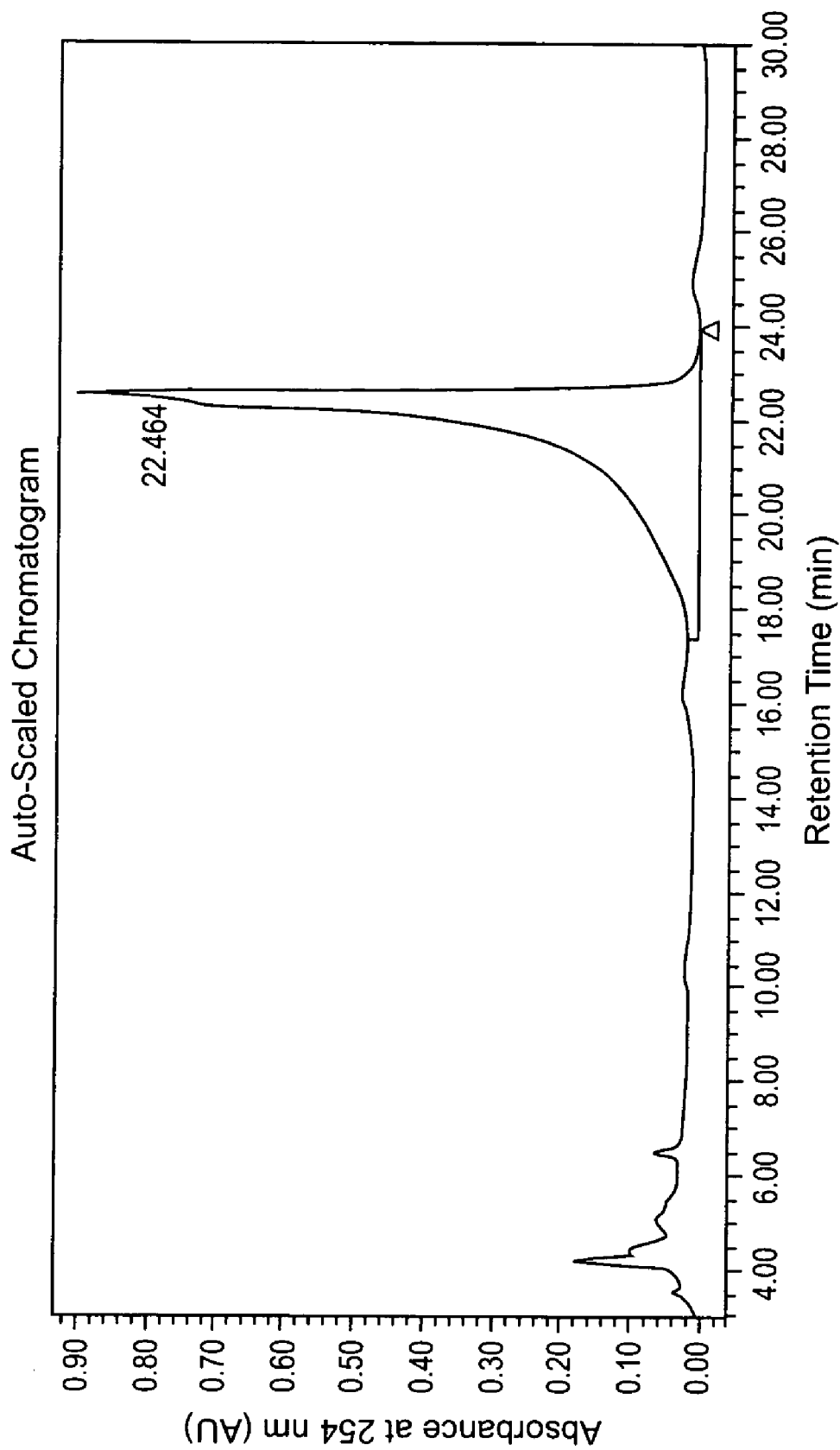
Figure 4B:
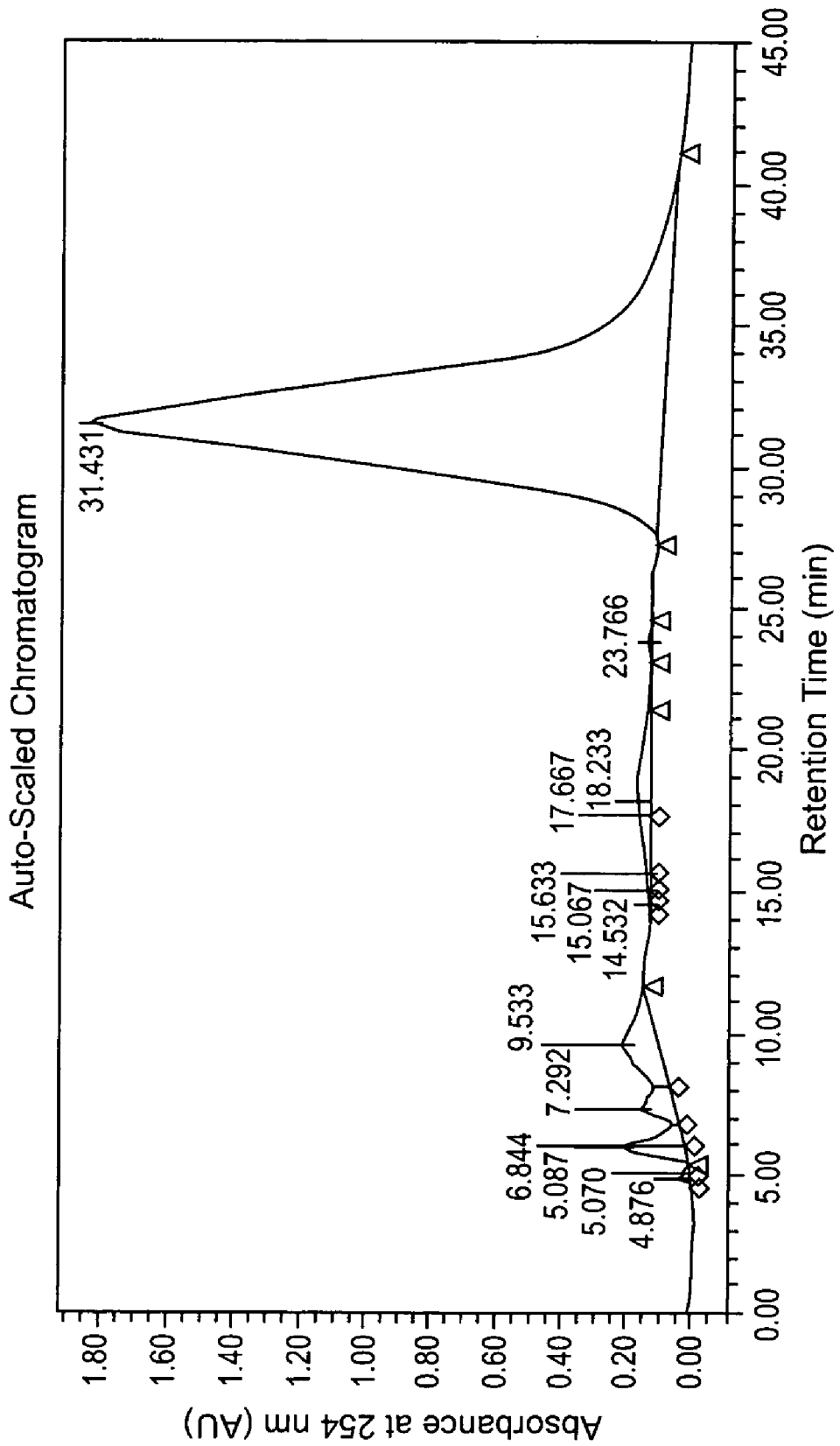
Figure 5A:
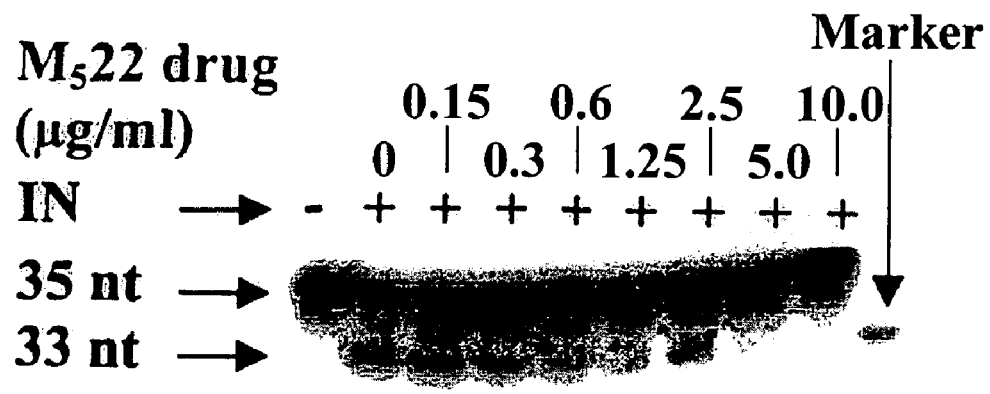
Figure 5B:
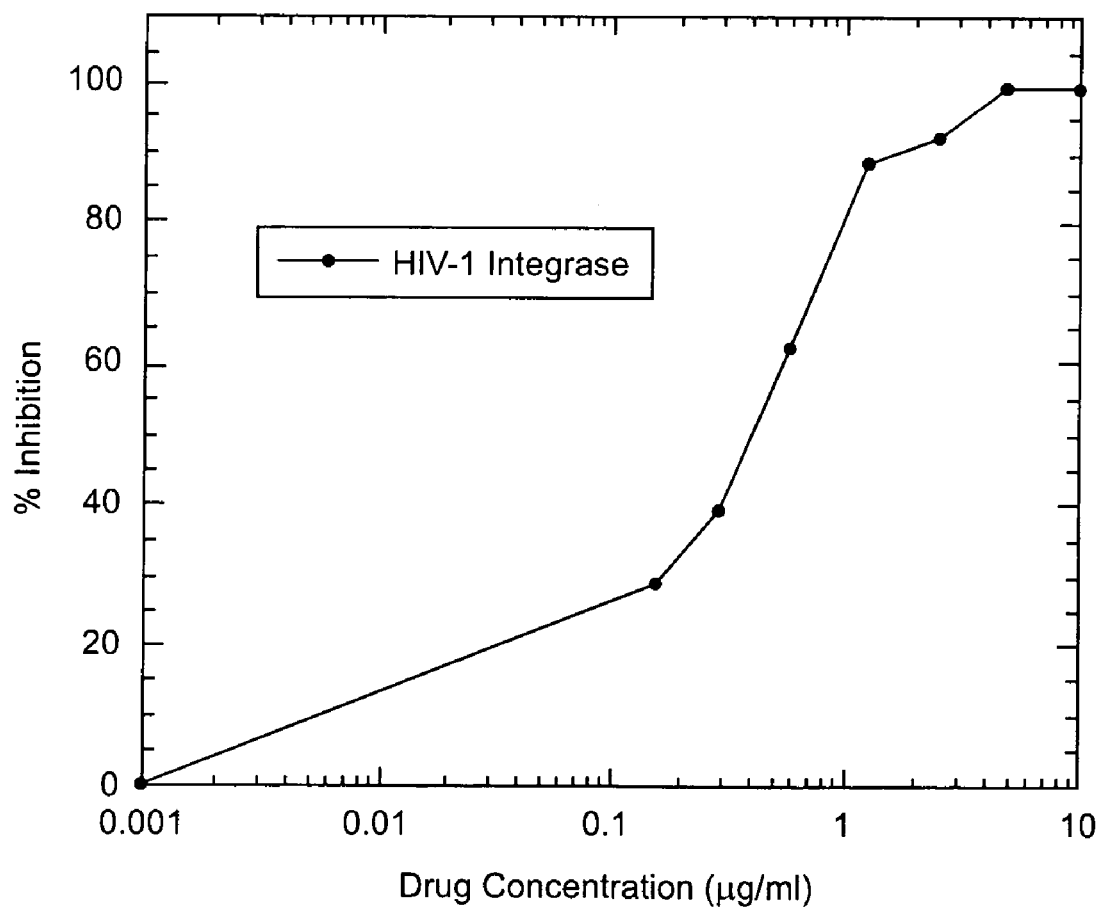
Figure 6A:
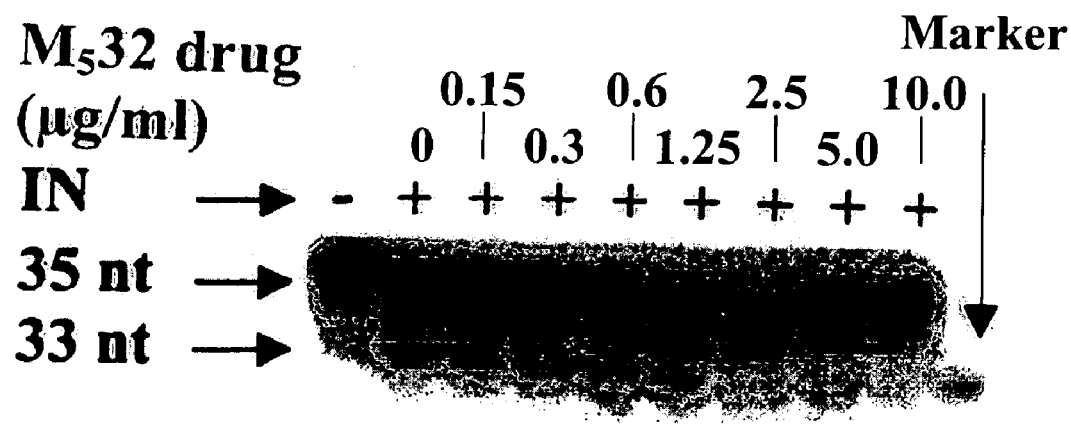
Figure 6B:
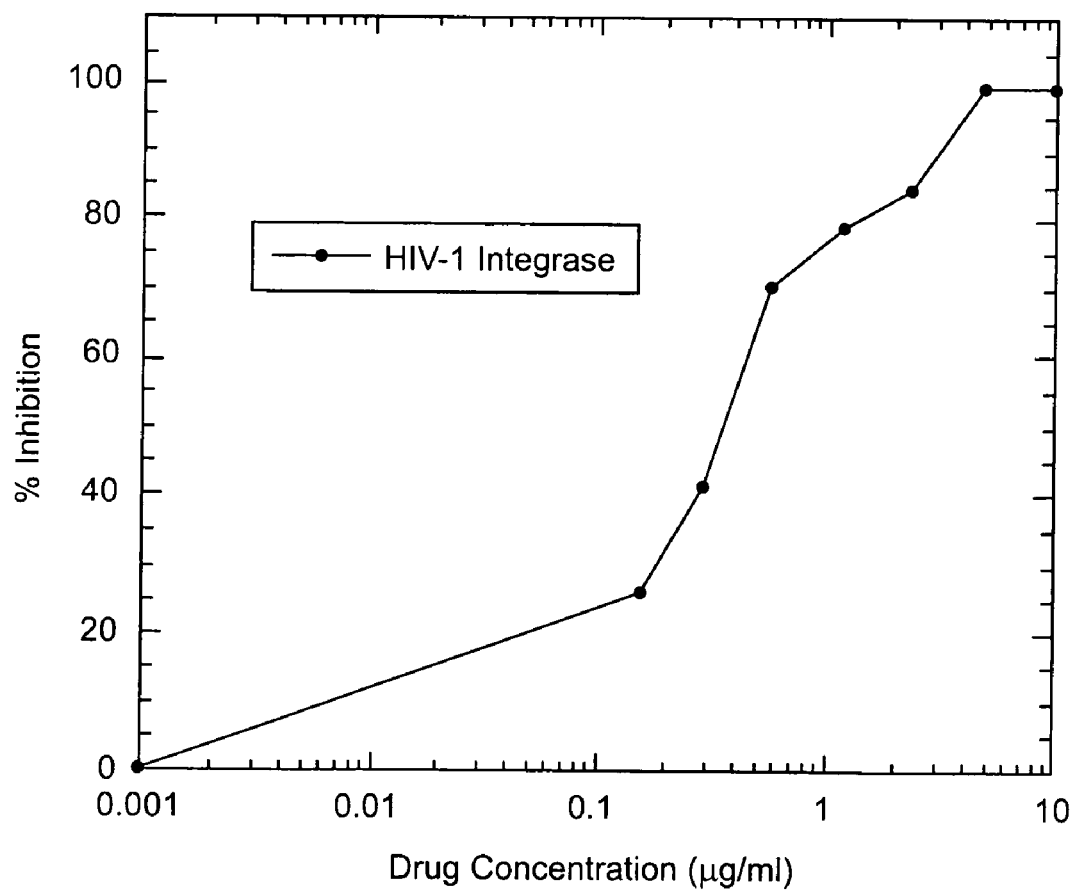
Figure 7A:
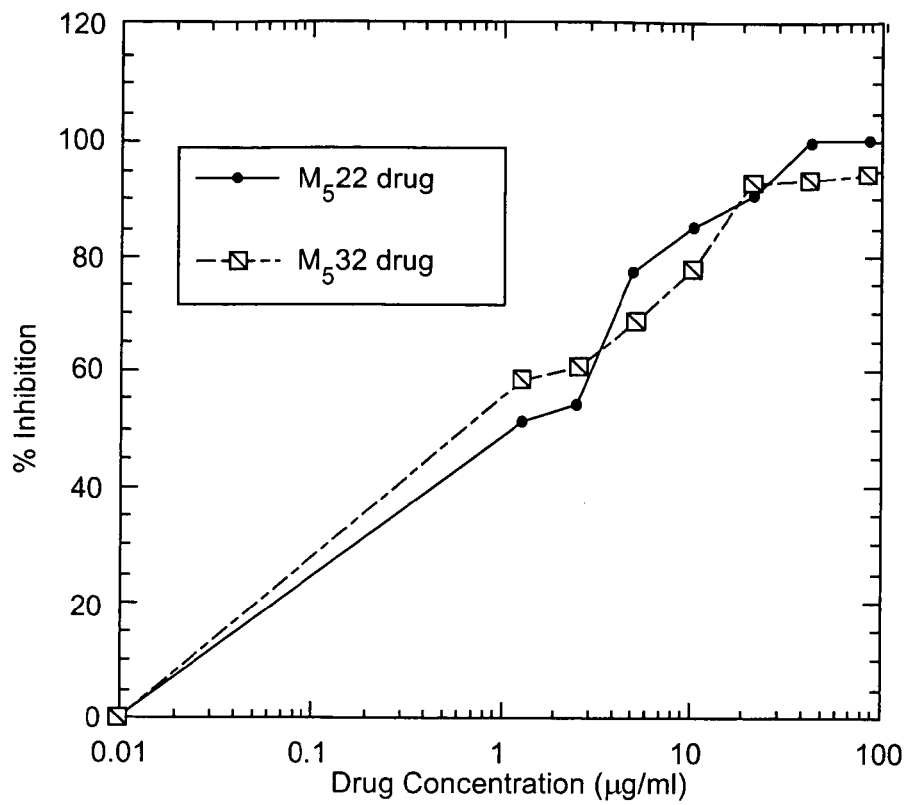
Figure 7B:
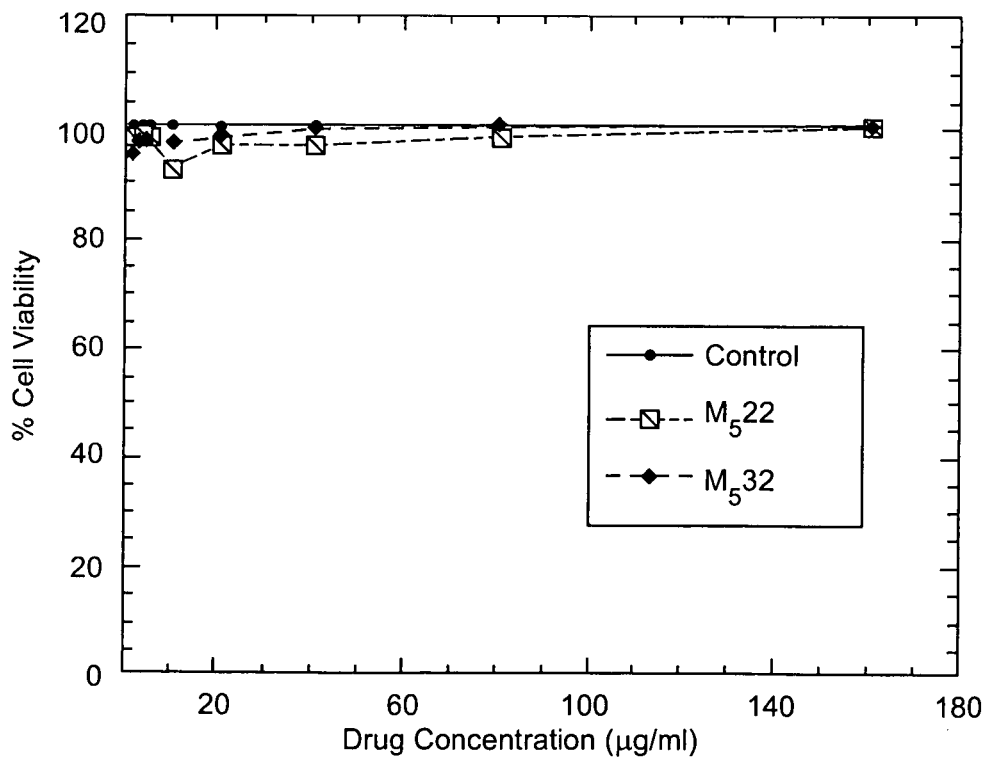
Figure 8:
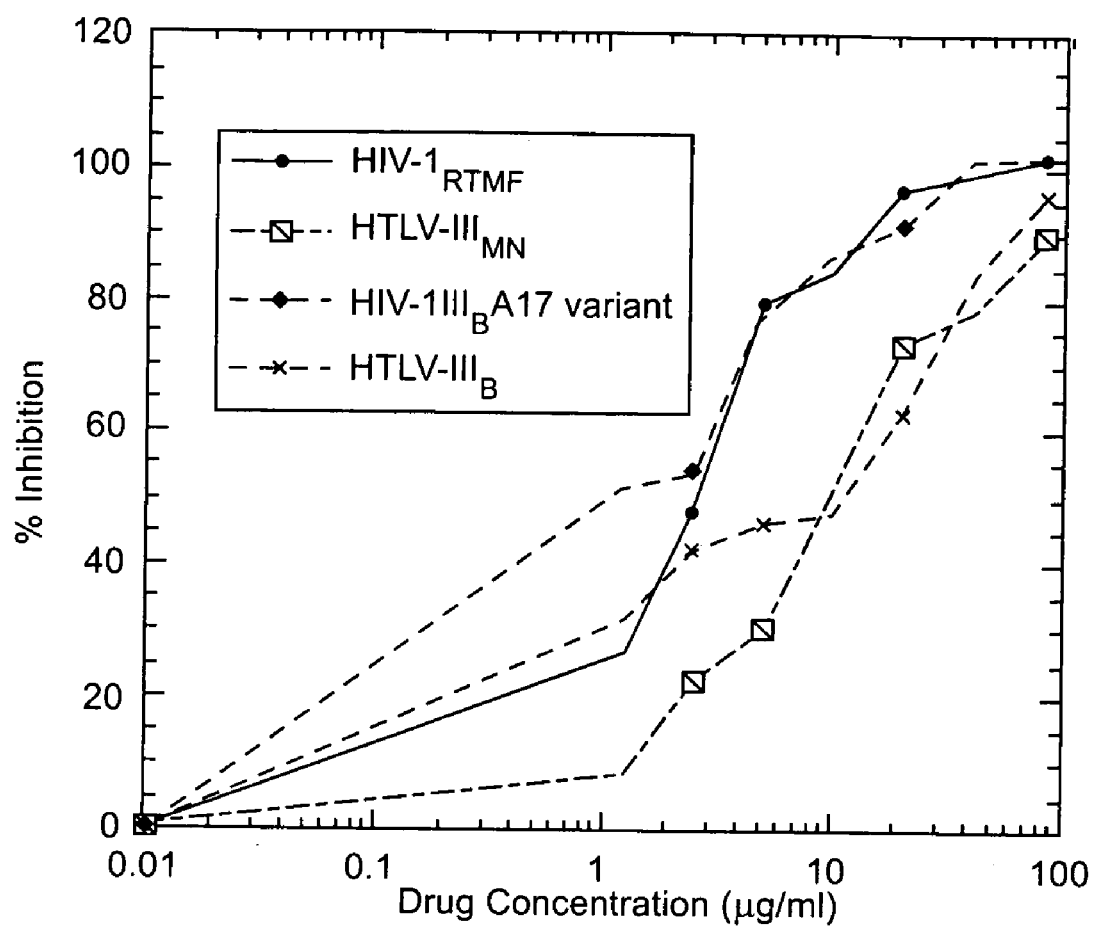

Having thus described the invention in general terms, reference will now be made to the accompanying drawings, wherein:

FIGS. 1A and 1B show the inhibition of 3' processing activities of HIV-1 integrase (IN) in the presence of varying concentrations of P.8s and P.8p fractions;

FIGS. 2A and 2B show the inhibition of 3' processing activities of HIV-1 integrase (IN) in the presence of different concentrations of butanol fraction ($Bu.M_5$);

FIG. 3 shows the HPLC chromatogram of the butanol fraction;

FIGS. 4A and 4B show the HPLC chromatograms of separately pooled $M_522$ and $M_532$ peaks from FIG. 3 reapplied to the column;

FIGS. 5A and 5B show the effect of $M_522$ compound on the inhibition of catalytic activities of HIV-1 integrase (IN) in the presence of different concentrations;

FIGS. 6A and 6B show the effect of $M_532$ compound on the inhibition of catalytic activities of HIV-1 integrase (IN) in the presence of different concentrations;

FIGS. 7A and 7B show the effect of $M_522$ and $M_532$ on HIV-1 replication and cell viability; and FIG. 8 shows the inhibition of HIV-1 replication on four different virus strains by using the $M_522$ compound in H9 cells.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terms "alkyl," "alkene," and "alkoxy" include straight chain and branched alkyl, alkene, and alkoxy, respectively. The term "lower alkyl" refers to C1–C4 alkyl. The term "alkoxy" refers to oxygen substituted alkyl, for example, of the formulas —OR or —$ROR^1$, wherein R and $R^1$ are each independently selected alkyl. The terms "substituted alkyl" and "substituted alkene" refer to alkyl and alkene, respectively, substituted with one or more non-interfering substituents, such as but not limited to, C3–C6 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like. The term "halogen" includes fluorine, chlorine, iodine and bromine.

"Aryl" means one or more aromatic rings, each of 5 or 6 carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents.

"Non-interfering substituents" are those groups that yield stable compounds. Suitable non-interfering substituents or radicals include, but are not limited to, halo, $C_1$–$C_{10}$ alkyl, $C_2$–$C_{10}$ alkenyl, $C_2$–$C_{10}$ alkynyl, $C_1$–$C_{10}$ alkoxy, $C_7$–$C_{12}$ aralkyl, $C_7$–$C_{12}$ alkaryl, $C_3$–$C_{10}$ cycloalkyl, $C_3$–$C_{10}$ cycloalkenyl, phenyl, substituted phenyl, toluoyl, xylenyl, biphenyl, $C_2$–$C_{12}$ alkoxyalkyl, $C_7$–$C_{12}$ alkoxyaryl, $C_7$–$C_{12}$ aryloxyalkyl, $C_6$–$C_{12}$ oxyaryl, $C_1$–$C_6$ alkylsulfinyl, $C_1$–$C_{10}$ alkylsulfonyl, —$(CH_2)_m$—O—($C_1$–$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$–$C_{10}$ alkyl), —C(O)—($C_1$–$C_{10}$ alkyl), $C_2$–$C_{10}$ thioalkyl, —C(O)O—($C_1$–$C_{10}$ alkyl), —OH, —$SO_2$, =S, —COOH, —$NR_2$, carbonyl, —C(O)—($C_1$–$C_{10}$ alkyl)-$CF_3$, —C(O)—$CF_3$, —C(O)$NR_2$, —($C_1$–$C_{10}$ alkyl)-S—($C_6$–$C_{12}$ aryl), —C(O)—($C_6$–$C_{12}$ aryl), —$(CH_2)_m$—O—$(CH_2)_m$—O—($C_1$–$C_{10}$ alkyl) wherein each m is from 1 to 8, —C(O)$NR_2$, —C(S)$NR_2$, —$SO_2NR_2$, —NRC(O)$NR_2$, —NRC(S)$NR_2$, salts thereof, and the like. Each R as used herein is H, alkyl or substituted alkyl, aryl or substituted aryl, aralkyl, or alkaryl.

The present invention is drawn to compounds and compositions which find use as antiviral agents. The present invention is also drawn to the method of isolating these compounds from plant extracts and using them to treat a variety of viral infections.

Due to the lack of toxicity and the low $IC_{50}$ values for inhibition of HIV-1 replication and HIV-1 integrase activity exhibited by the compounds of Formula (I) (See Examples), it is believed that purified compounds of Formula (I) are potent antiviral agents and can likely be useful as therapeutic drugs for AIDS, as well as other viruses.

The compounds and compositions of the invention have anti-viral activities. The phrase "antiviral activity" is used herein to mean the effective inhibition of the activity of a virus, including, but not limited to, its propagation or replication. Generally, virus replication includes cell entry, integration into the genome, transcription of the viral genome, translation of viral proteins, post-translational modifications, assembly of virion components, and release. Thus, the compositions of the invention effectively inhibit at least one aspect of the replication cycle. Assays can be performed to identify the mechanism by which the composition functions to inhibit viral activity. Such assays are well known in the art. See, for example, Lee et al. (1994) *Analytical Biochemistry* 220, 377–383; Lee et al. (1995) *Analytical Biochemistry* 227, 295–301; U.S. patent application Ser. No. 08/365,473; Lee et al. (1995) *Biochemistry* 34, 10205–10214; Lee et al. (1995) *Biochemistry* 34, 10215–10223; Lee and Han (1996) *Biochemistry* 35, 3837–3844.

The present invention encompasses purifying or isolating these antiviral compounds from plants. A purified or isolated compound is substantially free of other compounds. By "substantially free" is intended a purity of at least about 80%, 85%, 90%, 95%, 96%, 97%, 98%, 99%, or 99.5%. NMR profiles of samples of $M_522$ and $M_532$ compounds have confirmed a purity level of at least about 99 to 99.5%. By "purity" is intended the percentage of the dry weight of the compound of interest divided by the dry weight of the purified fraction containing the compound of interest.

The present invention also encompasses using compositions comprising such isolated compounds for the treatment of a variety of viral infections. By "treatment" is intended the either the reduction of the total number of viral particles, the retardation of viral propagation, or the relief or prevention of symptoms caused by viral infection in a patient following administration of these compositions. Assays can be performed to determine the inhibitory effect of a composition on viral activities, which include, but are not limited to, immunoassays detecting viral antigens, such as viral surface antigens or core antigens. Such assays are well known in the art.

The compositions of the invention comprise a purified compound of Formula (I):

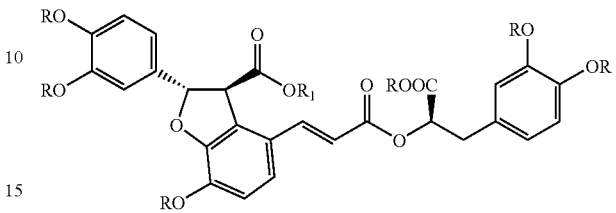

wherein:

each R is independently H or an alkyl group, such as a C1–C4 alkyl; and $R_1$ is H, alkyl, substituted alkyl, aryl or substituted aryl.

Preferred R substituents include H or methyl. Preferred $R_1$ substituents include alkyl groups substituted with a carboxyl group and a substituted phenyl ring, such as a phenyl ring substituted with one or more hydroxyl groups. In one preferred embodiment, $R_1$ and each R are H. In another embodiment, each R is H and $R_1$ is

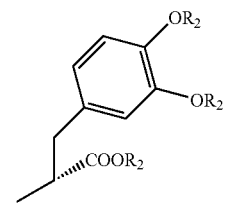

wherein each $R_2$ is independently H or alkyl, such as lower alkyl.

One preferred embodiment known as lithospermic acid (also referred to as $M_522$ herein), is shown below. The molecular weight of lithospermic acid is 538.

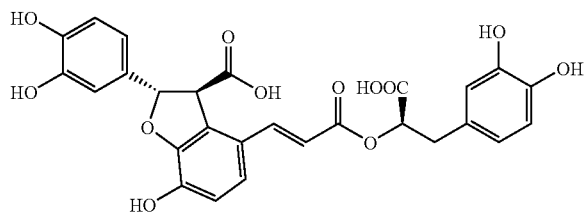

Lithospermic Acid ($M_522$)

(4-{2-[1-carboxy-2-(3,4-dihydroxy-phenyl)-ethoxycarbonyl]-vinyl}-2-(3,4-dihydroxy-pheny-7-hydroxy-2,3-dihydro-benzofuran-3-carboxylic acid)

Another preferred embodiment, known as lithospermic acid B (also referred to as $M_532$ herein), is shown below. The molecular weight of lithospermic acid B is 718.

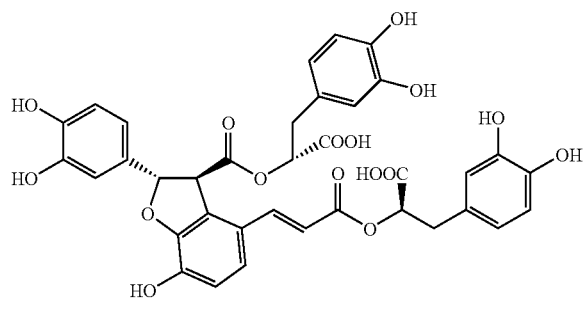

Lithospermic Acid B (M₅32)

(4-{2-[1-carboxy-2-(3,4-dihydroxy-phenyl)-ethoxy-carbonyl]-vinyl}-2-(3,4-dihydroxy-pheny-7-hydroxy-2,3-dihydro-benzofuran-3-carboxylic acid 1-carboxy-2-(3,4-dihydroxy-phenyl)-ethyl ester)

Viral integration is an attractive target because there is no apparent human protein counterpart, the steps involved in proviral integration are similar for all retroviruses, and the structural and functional properties among all types or classes of retroviral integrases are similar. See Khan et al. (1991) *Nucleic Acids Research* 19, 851–860; Thomas and Brady (1997) *Trends in Biotechnology* 15, 167–172. These publications are herein incorporated by reference. Thus, an inhibitor against integrase can be used as an antiviral therapy for a broad range of virus infections including HIV, SIV (simian immunodeficiency virus); MuLV (mouse leukemia virus); and the like.

Assays can be performed to test the inhibitory effect of a composition on the integration of the viral DNA into the host genome. For example, assays to test the ability of the composition to inhibit viral integrase activity are known in the art. Integrase specifically recognizes both ends of the viral DNA and removes two nucleotides from the 3' ends. The processed viral DNA and integrase then migrate to the nucleus where a viral integrase covalently links the viral genome to host chromosomal DNA, known as strand transfer, forming the provirus. Thus, inhibition of viral integrase results in inhibition of the integration of the viral DNA into the genome of the infected cells and the replication of the viral DNA. Thus, the level of integrase activity can be assayed by measuring the degree to which the ends of viral DNA or fragments containing viral DNA sequences are processed. It is recognized that the sequence of the DNA fragment used in the assay will vary according to the recognition specificity of the particular viral integrase that is being assayed. See Chow (1997) *Methods* 12, 306–317; Kulkosky et al. (1995) *Virology* 206, 448–456; Katzman and Katz (1999) *Advances in Virus Research* 52, 371–395. These publications are herein incorporated by reference. A compound that inhibits viral integrase activity can reduce the level of integrase activity by at least about 10%, 20%, 30%, 40%, 50%, 60%, 70%, 80%, 90%, 95%, 96%, 97%, 98%, or 99%.

The compositions of the invention can be used alone or in combination with other antiviral agents that inhibit the same or different aspects of the viral replication cycle (i.e., integration, viral entry, proviral transcription, viral replication, or viral assembly). Such agents include, but are not limited to, zidovudine (AZT), didanosine (ddI), stavudine (d4T), zalcitabine (ddC), amantadine interferon, ribavirin, rimantadine, and NDGA derivatives (See Gnabre, et al., 1995, *Proc. Natl. Acad. Sci.*, USA 92, 11239–11243; Hwu, et al., 1998, *J. Med. Chem.*, 41, 2994–3000; Chen, et al., 1998, *J. Med. Chem.*, 41, 3001–3007; U.S. Pat. No. 6,214,874 B).

The methods and compositions of the invention are useful against a wide array of viruses. For example, both simple and complex retroviruses are encompassed by the present invention. Members of those taxonomic divisions are set forth in Table 1.

TABLE 1

Major taxonomic divisions among retroviruses

| Category | Subgroup | Prototype | Other examples |
|---|---|---|---|
| Simple retroviruses | C-type retroviruses Group A | RSV | ALV, ASV |
| | C-type retroviruses Group B | MLV | FeLV, MSV, SNV, REV, SSV |
| | B-type retroviruses | MMTV | |
| | D-type retroviruses | MPMV | SRV-1 |
| Complex retroviruses | Lentiviruses | HIV-1 | HIV-2, SIV, visna virus, FIV, EIAV |
| | T-cell leukemia viruses | HTLV-1 | TLV-II, STLV, BLV |
| | Spumaviruses | HSRV | SFV, BFV |

Abbreviations: RSV, Rous sarcoma virus; ALV, avian leukemia virus; ASV, avian sarcoma virus; FeLV, feline leukemia virus; MSV, murine sarcoma virus; SNV, spleen necrosis virus; REV, reticuloendotheliosis virus; SSV, simian sarcoma virus; MMTV, mouse mammary tumor virus; MPMV, Mason-Pfizer monkey virus; SRV-1, simian retrovirus type 1; STLV, simian T-cell leukemia virus; BFV, bovine foamy virus The methods and compositions of the present invention are also useful in the treatment of diseases and/or clinical symptoms resulting from a viral infection. Such viral infections include, but are not limited to, infections caused by the complex group of retroviruses including all lentiviruses, spumaviruses as well as HTLV-1 and related viruses, which are responsible for diseases such as acquired immunodeficiency syndrome (AIDS) and T-cell leukemias (the human T lymphotrophic virus I, HTLV-I).

The antiviral compositions and compounds of the invention can be purified or partially purified from plants and plant extracts. Of particular interest are plants from the genus *Salvia*, such as *S. miltiorrhiza*, *S. officinalis*, *S. splendens*, *S. lyrata*, *urticifolia*, *S. farinace*, particularly *Salvia miltiorrhiza*. Of particular interest are extracts obtained from plant roots.

Methods are readily available for the partial purification or complete purification of the antiviral compound of the invention. Such methods include, for example, centrifugation, dialysis, solvent extraction (using solvent systems including methanol, dichloromethane, propanol, ethanol, butanol, etc.), precipitation, column separations, chromatography (liquid, anion exchange, cation exchange, thin layer, affinity, hydrophobic interaction, gel filtration, reverse phase, high performance liquid, etc.), mass spectrometry, and the like. Such methods can be used in any sequence or combinations. Generally, the antiviral compounds of the invention can be separated based on chemical and physical properties, such as solvent solubility, molecular size, charge, polarity, and hydrophobicity. For example, after an initial purification using dialysis, extraction and chromatography, tandem mass spectrometry (MS/MS) can be performed on the sample extract. MS/MS is utilized when mixtures contain components of the same molecular weight. Likewise, LS/MS/MS is a powerful tool for characterizing samples with large numbers of components.

Methods for such procedures are readily available in the prior art. See, for example, *Perry's Chemical Engineers' Handbook*, Sixth Ed. (Robert H. Perry and Don Green (eds.)) McGraw-Hill, Inc. (1984); *Practical HPLC methodology and applications* (Brian A. Bidlingmeyer) 1992 Wiley, N.Y.; *A Practical guide to HPLC detection* (edited by Donald Parriott) 1993 Academic Press, Inc., San Diego, Calif.; *Solvent extraction in analytical chemistry* (George H. Morrison and Henry Freiser) 1957 Wiley N.Y.; *Solvent extraction in biotechnology: recovery of primary and secondary metabolites* (Karl Schugerl) 1994 Springer-Verlag Berlin, N.Y.; *Interpretation of mass spectra of organic compounds* (Mynard C. Hamming and Norman G. Foster) 1972 Academic Press, Inc. New York; Youngquist et al. (1995) *J. Am. Chem. Soc.* 117: 3900–3906; Dunayevskiy et al (1995) *Anal. Chem.* 67: 2906–2915; Brummel et al. (1996) *Anal. Chem.* 68: 237–242; Metzger et al. (1994) *Analytical Biochemistry* 219: 261–277; Brummel et al. (1994) *Science* 264: 399–402; *Methods in Enzymology*, Vol. 182, *Guide to Protein Purification*, edited by Murray P. Deutscher 1990, Academic Press, Inc. San Diego, Calif.; herein incorporated by reference.

In a preferred method, the compounds of the invention are isolated or purified from plant material, such as *Salvia miltiorrhiza*. The preferred method comprises extracting an alcohol-soluble fraction from the plant material, such as a root material. A group of compounds are then precipitated from the alcohol-soluble fraction and separated into an aqueous layer and an organic layer, such as a butanol-soluble layer. Thereafter, chromatography techniques can be used to isolate at least one compound of Formula (I) from the organic layer. For example, high performance liquid chromatography (HPLC) can be used in the isolation step.

At each stage of the purification process, the resulting fractions can be tested for antiviral activity. In this manner, partially purified extracts, extracts containing at least the active compound of Formula (I), a partially purified compound of Formula (I), or an isolated compound of Formula (I) having antiviral activity can be obtained. Antiviral activity can be tested using standard techniques such as the integrase assay set forth in the Experimental Section or others known in the art.

After purification of antiviral compounds by the methods noted above, various methods are available in the art for the determination of the structure of the isolated compounds; for example, mass spectroscopy and nuclear magnetic resonance (NMR), and the like.

The purified antiviral compounds can be administered in various compositions to a population of cells that are infected with the virus. The population of cells can be cultured in vitro, or found in vivo in a living organism, more particularly a mammal. In vitro, the population of cells can be adherent cells or cells in suspension. In vivo, the population of cells can be from any organ or combination of organs of the body of the organism.

The antiviral compositions can be used for the treatment of patients infected with a virus or viruses, when the compositions of the present invention has an inhibitory effect on the activity of such virus. All viral infections in patients are potentially treatable by the composition in the present invention.

The antiviral compositions can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences* (16 th ed., Osol, A. (ed.), Mack, Easton Pa (1980)). In order to form a pharmaceutically acceptable composition suitable for effective administration, such compositions will contain an effective amount of the antiviral compound, either alone, or with a suitable amount of carrier vehicle.

Additional pharmaceutical methods may be employed to control the duration of action. Controlled release preparations may be achieved by the use of polymers to complex or absorb the antiviral compositions. The controlled delivery may be exercised by selecting appropriate macro molecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in *Remington's Pharmaceutical Sciences* (1980).

It is contemplated that the inhibitory compositions of the present invention will be administered to an individual in therapeutically effective amounts. That is, in an amount sufficient to inhibit the replication and/or propagation of the target virus. The effective amount of the inhibitory composition will vary according to the weight, sex, age, and medical history of the individual. Other factors which influence the effective amount may include, but are not limited to, the severity of the patient's condition, the severity of viral infection, the stability of the antiviral compound, the kinetics of interaction between the virus and the antiviral compound, previous exposure to the inhibitory compound, kidney or other disease, etc. An effective amount can reduce the level of virus activity by about 10%, 20%, 30%, 40%, 50%, 60%, 70%, 80%, or 90%, preferably about 95%, 96%, 97%, or 98%, more preferably about 99%. Typically, a therapeutically effective amount will range from about 0.1 mg to about 300 mg per kg of body weight per day.

The pharmaceutically prepared inhibitory compositions of the invention may be provided to a patient by means well known in the art. Such means of introduction include oral means, intranasal means, subcutaneous means, intramuscular means, intravenous means, intraarterial means, or parenteral means.

The antiviral compounds of the present invention may be dissolved in any physiologically tolerated liquid in order to prepare an injectable bolus. It is generally preferable to prepare such a bolus by dissolving the molecule in normal saline.

Thus, the present invention provides a method of treating AIDS in a subject, comprising administering to the subject an effective amount of a compound of the present invention, such as a compound of Formula (I). The administering step can comprise administering an effective amount of the compound in a pharmaceutically acceptable carrier.

For the purposes of AIDS therapy, a compound of Formula (I) is administered to the subject in an amount sufficient to inhibit HIV-1 from further infecting other cells.

However, the therapeutically effective dosage of any specific compound will vary somewhat from compound to compound, patient to patient, and will depend upon the condition of the patient and the route of delivery. When administered conjointly with other pharmaceutically active agents, even less of the compounds of Formula (I) may be therapeutically effective. The compound of Formula (I) may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

The compounds of Formulas (I) may be administered per se or in the form of a pharmaceutically acceptable salt. When used in medicine, the salts of the compounds of Formulas (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of a compound of Formula (I) with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulphonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of the carboxylic acid group.

Thus the present invention also provides pharmaceutical formulations or compositions, both for veterinary and for human medical use, which comprise the a compound of Formula (I) or a pharmaceutically acceptable salt thereof with one or more pharmaceutically acceptable carriers thereof and optionally any other therapeutic ingredients, such as other chemotherapeutic agents for AIDS. The carrier(s) must be pharmaceutically acceptable in the sense of being compatible with the other ingredients of the formulation and not unduly deleterious to the recipient thereof.

The compositions includes those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier or both, and then, if necessary, shaping the product into desired formulations.

Compositions of the present invention suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parental administration conveniently comprise a sterile aqueous preparation of the active compound, which can be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

Further, the present invention provides liposomal formulations of the compounds of Formula (I) and salts thereof. The technology for forming liposomal suspensions is well known in the art. When the compound of Formula (I) or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer that forms the structure of the liposome. In either instance, the liposomes that are produced may be reduced in size, as through the use of standard sonication and homogenization techniques. The liposomal formulations containing the compounds of Formula (I) or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula (I) or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts.

In addition to the aforementioned ingredients, the compositions of the invention may further include one or more accessory ingredient(s) selected from the group consisting of diluents, buffers, flavoring agents, binders, disintegrants, surface active agents, thickeners, lubricants, preservatives (including antioxidants) and the like.

Having now generally described this invention, the same will be better understood by reference to certain specific examples which are included herein for purposes of illustration only, and are not intended to be limiting of the invention, unless specified.

Experimental

The plant, *Salvia miltiorrhiza*, (SM), has been recorded in the Chinese traditional medical book "Ben-cao-gan-mu" with the function of "to activate blood and to resolve stagnant." It showed multiple pharmacological activities both in vitro and in vivo. Its preparations have been used safely to treat cardiovascular and liver diseases for generations. The herb is widely distributed in China with different species in different districts.

In the appended examples, purification and testing of active anti-HIV compounds from crude extracts of *Salvia miltiorrhiza* roots is described. Two potent, non-toxic HIV-1 integrase inhibitors, $M_522$ and $M_532$, were isolated using high performance liquid chromatography (HPLC). Both are pure compounds that showed strong anti-HIV activity in infected H9 cells.

The following cells and virus strains were obtained from the AIDS Research and Reference Regent Program, Division of AIDS, National Institute of Allergy and Infectious Diseases: H9 cells, virus strains of HIV-$1_{IIIB}$A17, a variant resistant to RT nonnucleotide inhibitors and HIV-$1_{L10R/M461/L63P/V82T/184V}$, a protease inhibitor resistant virus, as well as viral strains HTLV-III$_{mn}$, HIV-$1_{RTMF}$ and HTLV-III$_B$. Virus-infected H9 cells were cultured in the presence of different concentrations of $M_522$ and $M_532$ and viral replication was assayed using the HIV/p24 monoclonal antibody assay.

The HIV-1 integrase assay utilized in testing described below used a DNA substrate consisting of a DNA sequence derived from the U5 end of HIV-1 LTR. It was prepared by annealing oligonucleotide U5V1 (5'-GACCCTTTTAGT-CAGTGT GGAAAATC TCTAGCAGT) with its complementary strand U5V2 (3'-CTGGGAAAATCAGTCACAC-CTTTTAGAGATCGTCA). The U5V1 strand was labeled at the 5'-end with [γ-$^{32}$P] ATP using T4 polynucleotide kinase as described previously (Kamata et al., 1994). The standard reaction mixture included reaction buffer (40 mM HEPES, pH 7.5, 20 mM MnCL$_2$, 60 mM NaCl, 20 mM DTT and 0.1% Nonidet-P40) and HIV-1 integrase (NIH AIDS Research and Reference Reagent Program). To assay for 3'-end processing, the labeled substrate was incubated with the reaction mixture for 60 minutes at 37° C. An equal volume of stop solution (95% formamide, 30 mM EDTA, 0.1% xylene cyanol, 0.1% bromophenol blue) was added to each reaction and the samples were heated to 95°' C. for 5 minutes to denature the DNA. The samples were then fractionated by electrophorsis on a 15% denaturing polyacrylamide gel. The 3'-end processing activity was monitored by the appearance of a radioactive oligonucleotides product (33 nt), shortened by two nucleotides from the original substrate (35 nt). The products were visualized by autoradiography and quantitation was carried out by phosphorimaging.

EXAMPLE 1

Isolation and Testing of Propanol Soluble (P.8s) and Precipitate (P.8p) Fractions from *Salvia miltiorrhiza* roots Root powder (1.5 kg) of *Salvia miltiorrhiza* (supplied by Jiang Su Danhua Group Co., China) was extracted three times with 4.5 liters of 70% methanol for 24 hours each time with vigorous shaking. The three extracts (70 S fraction) were combined, evaporated to dryness and dissolved in 2.0 liters of 25% NH$_4$OH. The extract solution was then precipitated with four volumes of 1-propanol and the precipitate was washed three times with 5.0 liters of P.8 buffer (Propanol: H$_2$0: NH$_4$OH, 80:15:5). Both the propanol soluble (P.8s) and precipitate (P.8p) fractions were tested for anti-HIV integrase activity.

The results of testing are shown in FIGS. 1A and 1B. The 3'-end processing product catalyzed by HIV-1 integrase (33 nt) and the DNA substrate (35 nt) are shown. In FIG. 1A, different concentrations of supernatant fraction (P.8s) were tested with HIV-1 integrase: lane 1, without integrase (IN); lane 2, integrase (IN) alone; lanes (3–5) integrase with 0.25, 0.5 and 1.0 μg/ml of P.8s fraction; lane 6, 33 nucleotide marker. In FIG. 1B, the 3'-end processing activity of HIV-1 integrase was assayed with the precipitate fraction (P.8p): lane 1, without integrase (IN); lane 2, integrase (IN) alone; lanes (3–12) integrase with 0.006, 0.012, 0.025, 0.05, 0.1, 0.2, 0.4, 0.6, 0.8 and 1.0 μg/ml of P.8p and lane 13, 33 nucleotide marker. The P.8 precipitate (p.8p), which represented approximately 34% of the root material, showed potent anti-HIV integrase activity in the 3' cleavage activity assay with an IC$_{50}$ of 0.1 μg/ml while the P.8 soluble fraction (P.8s), representing 66% of the starting material was relatively less active (IC$_{50}$=1 μg/ml).

To evaluate the potential clinical value of the P.8p fraction, intraperitoneal acute and subacute toxicity tests in mice were conducted for seven days, where P.8p was given once each day for the acute test and twice each day for the subacute test. The toxicity tests for the P.8p fraction were conducted in kunming mice (body weight, 20±1 gm) over a period of seven days. For the acute toxicity test, groups of 10 mice were given doses of 0.45, 0.69, 0.98, 1.60 and 2.00 g/kg once each day and for the subacute toxicity test, mice were given doses of 0.1, 0.2, 0.4 g/kg twice each day.

The number of mouse deaths were recorded daily and LD$_{50}$ was calculated on the 7$^{th}$ day (see Table 2 below). The results showed that the LD$_{50}$ of the P.8p fraction was 1.2 g/kg for the acute toxicity test and 0.18 g/ kg for the subacute toxicity test. The P.8p extract showed cumulative toxicity in mice when given intraperitoneally in multiple doses. Thus, although the P.8p fraction contained highly active HIV integrase inhibitors, it also contained materials toxic to animals that should be removed.

TABLE 2

Acute and Subacute Toxicity Tests of the P.8p Fraction in Mice

| Toxicity Test | Administration Route | Dosage (g/kg) | No. mice | Mortality (7$^{th}$ day) | LD$_{50}$ (g/kg) (7$^{th}$ day) |
|---|---|---|---|---|---|
| Acute* | IP | 2.00 | 10 | 10/10 | 1.20 |
|  |  | 1.60 | 10 | 8/10 |  |
|  |  | 0.98 | 10 | 4/10 |  |
|  |  | 0.69 | 10 | 0/10 |  |
|  |  | 0.45 | 10 | 0/10 |  |

TABLE 2-continued

Acute and Subacute Toxicity Tests of the P.8p Fraction in Mice

| Toxicity Test | Administration Route | Dosage (g/kg) | No. mice | Mortality (7th day) | LD$_{50}$ (g/kg) (7th day) |
|---|---|---|---|---|---|
| Subacute** | IP | 0.40 | 10 | 10/10 | 0.18 |
| | | 0.20 | 10 | 6/10 | |
| | | 0.10 | 10 | 0/10 | |

*P.8p was given once each day
**P.8p was given twice each day

EXAMPLE 2

Isolation and Testing of Butanol Fraction (Bu.M$_5$) from P.8p Fraction

To separate these toxic materials from the antiviral components, a second purification step was employed. For further purification of the P.8p fraction, 50 grams were dissolved in 200 ml of NAA buffer (7% acetonitrile, O.1M of ammonium acetate; 0.5% acetic acid) and the cleared NAA fraction was next mixed with 200 ml of 1-butanol and shaken vigorously. The mixture was partitioned into an NAA layer and a butanol layer, which were collected separately. The butanol (Bu.M$_5$) fraction was dried, redissolved in 5% methanol, cleared by centrifugation and then dried again.

The anti-HIV integrase activity of Bu.M$_5$ was tested. The 3'-end processing product catalyzed by HIV-1 integrase (33 nt) and the DNA substrate (35 nt) are shown in FIGS. 2A and 2B. In FIG. 2A, different concentrations of the Bu.M$_5$ fraction were tested with HIV-1 integrase: lane 1, without integrase (IN); lane 2, integrase (IN) alone; lanes (3–9) integrase with 0.08, 0.16, 0.3, 0.6, 1.25, 2.5 and 5.0 µg/ml of Bu.M$_5$. In FIG. 2B, the percent inhibition of HIV-1 integrase activity with increasing concentrations of Bu.M$_5$ fraction is illustrated. The IC$_{50}$ of this fraction is 0.6 µg/ml. Thus, anti-HIV integrase activity was evident (yield<1%) in the combined butanol extracts (Bu.M$_5$).

The toxicity of the Bu.M$_5$ fraction was tested in C57bl/6 mice by tail vein injections of the Bu.M$_5$ fraction (2 mg/ml in 0.9% NaCl) over a period of seven days at a daily dose of 10 mg/kg, 20 mg/kg and 30 mg/kg, using two mice per dosage group. The Bu.M$_5$ fraction showed no toxicity in C57bl/6 mice, with no weight loss observed after tail vein injections of 10 mg–30 mg/kg each day for seven days. Thus, it is believed that the butanol-soluble fraction of the P.8p fraction would also be useful as an antiviral agent.

EXAMPLE 3

Purification, Identification and Testing of HIV-integrase Active Compounds from Bu.M$_5$ Fraction A. Isolation of Active Compounds High performance liquid chromatography (HPLC) was used to further purify the Bu.M$_5$ fraction and to isolate pure anti-HIV compounds from *S. miltiorrhiza* roots. A limited amount (100 mg) of butanol fraction (Bu.M$_5$) was used for each run. HPLC was performed on Waters liquid chromatograph equipped with two 510 pumps and a 996 photodiode array detector. The extract solution was separated and analyzed by using a 250×10 mm. preparative C18 (8µm) column with the mobile phase consisting of 5% methanol. The flow rate was 1.0 ml/min and the elution was monitored at a wavelength of 254 nm to facilitate the detection of the different compounds. FIG. 3 is a HPLC chromatogram of the Bu.M$_5$ fraction. Many peaks were resolved at different retention times. The activity of each one was tested against HIV-1 integrase activity to identify the active compounds.

Two major peaks with retention times of 22.4 minutes and 31.4 minutes (M$_5$22 and M$_5$32) were well separated from a large, exceedingly complex mixture of unresolved compounds. These two major peaks were separately pooled and then reapplied to the column. FIGS. 4A and 4B are the HPLC chromatograms of separately pooled M$_5$22 and M$_5$32 peaks from FIG. 3 that were reapplied to the column. FIG. 4A shows a single and major peak (M$_5$22) was eluted at 22.4 retention time. FIG. 4B shows one major peak (M$_5$32) that eluted at about 31.4 retention time. Both M$_5$22 and M$_5$32 were found to be 99%+ pure compounds by NMR analysis.

Approximately 500 runs were made to isolate M$_5$22 and M$_5$32. The yield for M$_5$22 and M$_5$32 from the Bu.M$_5$ fraction was approximately 13% and 26%, respectively. An overall yield from the initial *Salvia miltiorrhiza* roots of 0.018% and 0.038% for M$_5$22 and M$_5$32 was obtained. A brief summary of the purification and the HPLC profiles for compounds M$_5$22 and M$_5$32 are shown in Table 3 below.

TABLE 3

A summary of the Purification of HIV-1 Inhibitors from *S. miltiorrhiza* Roots

| | Fraction | Amount (g) | Yield (%) |
|---|---|---|---|
| | *S. miltiorrhiza* roots | 1500 | |
| Step I | P.8p | 516 | 34.4 |
| Step II | Bu.M$_5$ | 2.2 | 0.15 |
| Step III | HPLC pure compounds: | | |
| | M$_5$22 | 0.277 | 0.018 |
| | M$_5$32 | 0.572 | 0.038 |

B. Identification of Isolated Compounds

The structures of M$_5$22 and M$_5$32 were identified by NMR and MS analysis using known structural standards for comparison (Tanaka et al., 1989). M$_5$22 was identified as lithospermic acid: (4-{2-[1-carboxy-2-(3,4-dihydroxy-phenyl)-ethoxycarbonyl]-vinyl}-2-(3,4-dihydroxy-phenyl)-7-hydroxy-2,3-dihydro-benzofuran-3-carboxylic acid). M$_5$32 was identified as lithospermic acid B: (4-{2-[1-carboxy-2-(3,4-dihydroxy-phenyl)-ethoxycarbonyl]-vinyl}-2-(3,4-dihydroxy-phenyl)-7-hydroxy-2,3-dihydro-benzofuran-3-carboxylic acid 1-carboxy-2-(3,4-dihydroxy-phenyl)-ethyl ester).

C. Efficacy Testing of Isolated Compounds

The anti-HIV efficacy of the two isolated compounds was analyzed by their effect on the 3' processing activity assay and their inhibition of HIV in cultured H9 cells. The inhibitory data indicate that the two compounds are highly potent against HIV integrase, with IC$_{50}$ of 0.45 µg/ml, 0.83 µM for M$_5$22 and 0.35 µg/ml, 0.45 µM for M$_5$32. These results are illustrated in FIGS. 5 and 6.

FIGS. 5A and 5B illustrate the effect of M$_5$22 on the inhibition of HIV-1 integrase (IN) activity in the presence of different concentrations. In FIG. 5A, the 3'-end processing product catalyzed by HIV-1 integrase (33 nt) and the DNA substrate (35 nt) are shown: lane 1, without integrase (IN); lane 2, integrase (IN) alone; lanes (3–9) integrase with 0.15, 0.3, 0.6, 1.25, 2.5, 5.0, and 10 µml of M$_5$22 and lane 10, 33 nucleotide marker. FIG. 5B is a quantitation of assay results by phosphorimager showing a dose-response curve for the inhibition of HIV-1 integrase activity by the $M_s22$ compound. The $IC_{50}$ of $M_s22$ is 0.45 µg/ml, 0.83 µM.

FIGS. 6A and 6B illustrate the effect of $M_s32$ on the inhibition of HIV-1 integrase (IN) activity in the presence of different concentrations. In FIG. 6A, the 3'- end processing product catalyzed by HIV-1 integrase (33 nt) and the DNA substrate (35 nt) are shown: lane 1, without integrase (IN); lane 2, integrase (IN) alone; lanes (3–9) integrase with 0.15 0.3, 0.6, 1.25, 2.5, 5.0, and 10 µg/ml of $M_s32$ and lane 10, 33 nucleotide marker. FIG. 6B is a quantitation of assay results by phosphorimager showing a dose-response curve for the inhibition of HIV-1 integrase activity by the $M_s32$ compound. The $IC_{50}$ of $M_s32$ is 0.35 µg/ml, 0.45 µM.

The inhibitory effect of $M_s22$ and $M_s32$ against HIV replication was further examined using HIV-$1_{IIIB}A17$, a variant resistant to RT nonnucleotide inhibitors and HIV-$1_{L10R/M461/L63P/V82T/184V}$, a protease inhibitor resistant virus, as testing viruses in the presence of a variety of drug concentrations in infected H9 cells. By using the HIV/p24 monoclonal antibody assay, the $IC_{50}$ for $M_s22$ and $M_s32$ against HIV replication were found to be 1.5 µg/ml, 2.7 µM for $M_s22$ and 1 µg/ml, 1.39 µM for $M_s32$.

FIG. 7A graphically illustrates the effect of $M_s22$ and $M_s32$ on HIV-1 replication. FIG. 7A illustrates the dose-dependent inhibition of HIV-1 replication in H9 cells infected with HIV-$1_{IIIB}A17$ and HIV-$1_{L10R/M461/L63P/V82T/184V}$ viruses in the presence of different drug concentrations of $M_s22$ and $M_s32$. Viral replication was measured using the HIV/p24 monoclonal antibody assay and the $IC_{50}$ values for inhibition by $M_s22$ and $M_s32$ against HIV replication were calculated as 2.7 µM and 1.39 µM respectively.

D. Cytotoxicity of Isolated Compounds

The cytotoxicity of $M_s22$ and $M_s32$ drugs against H9 cells was analyzed using MTT [3-(4,5-dimethylthiazol-2-yl)-2,5-diphenyltetrazolium bromide] assay (Sigma Chemical Co.) (Uckun et al., 1998). Briefly, exponentially growing H9 cells were seeded onto 96-well plates at a density of $3 \times 10^4$ cells/well and incubated for 24 h at 37° C. prior to drug exposure. On the day of treatment, a series Of $M_s22$ and $M_s32$ concentrations (1.25, 2.5, 5, 10, 20, 40, 80, and 160 µg/ml) were used to test their cytotoxicity in H9 cells. Quadruplicate wells were used for each treatment. The cells were incubated with $M_s22$ and $M_s32$ for 4 days at 37° C. in a humidified 5% $CO_2$ atmosphere. To each well, 50 µl of MTT (1 mg/ml final concentration) was added and the plates were incubated at 37° C. for 4 h to allow MTT to form formazan crystals by reacting with metabolically active cells. The formazan crystals were solubilized with DMSO. The absorbance of each well was measured in a microtiter reader at optical density 540 nm. The reaction is specific, no significant amounts of formazan can be detected with dead cells. We found that the cells remained viable even at the highest concentrations ($CC_{100}$) of $M_s22$ and $M_s32$ tested (160 µg/ml, 297 µM for $M_s22$ and 160 µg/ml, 223 µM for $M_s32$), indicating that both compounds are non-toxic. These results are presented graphically in FIG. 7B.

EXAMPLE 4

$M_s22$ and $M_s32$ Inhibit the Replication of Four Different Virus Strains in Human H9 Cells Inhibitory activity of $M_s22$ and $M_s32$ against the replication of four different HIV-1 strains was tested in this example. Two of the strains were drug-resistant virus isolates (HIV-$1_{RTMF}$ resistant against AZT and HIV-$1_{IIIB}A17$ variant resistant against inhibition by RT nonnucleotide inhibitors) and the other two were primary isolates (HTLV-$III_{MN}$ and HTLV-$III_B$).

On the day before infection, H9 cells were subcultured at $1-2 \times 10^5$ cells/ml and on the day of the infection, cells were pelleted by centrifugation at room temperature for 10 minutes. The pellet was then resuspended with 1 ml of each strain according to the virus titer. The mixtures were incubated at 37° C. in $CO_2$ incubator for 2 hours. The cells were then washed two times with PBS and then two times with the culture medium (RPMI 1640). The cells were resuspended with fresh medium and plated in 96 well plates. Every 3–4 days after infection, cells were sub-cultured and supernatant was saved to assay for virus production.

The activity of $M_s22$ against the four strains were tested at various drug concentrations of 80, 40, 20, 10, 5, 2.5, 1.25, and 0 µg/ml. After 8 days, the infection of the cells was detected by using HIV-1 p24 antigen assay, which is an enzyme immunoassay (EIA, or enzyme-linked immunosorbent assay) developed for detection and quantitation of the HIV-1 p24 core protein. The percentage of HIV-1 inhibition achieved by the different concentrations of $M_s22$ are shown in Table 4 below. The $IC_{50}$ of $M_s22$ for HIV-$1_{RTMF}$, HIV-1 $III_BA17$, HTLV-$III_B$ and HTLV-$III_{MN}$ were 2.7 µg/ml, 1.5 µg/ml, 11 µg/ml, and 9 µg/ml, respectively. These results are illustrated graphically in FIG. 8.

TABLE 4

Inhibition of Four Strains HIV-1 Replication by $M_s22$ Drug

| | % Inhibition | | | |
|---|---|---|---|---|
| | HIV-$1_{RTMF}$ | HTLV-$III_{MN}$ | HIV-$III_BA17$ VARIANT | HTLV-$III_B$ |
| 00. µg/ml | 0.0 | 0.0 | 0.0 | 0.0 |
| 1.25 µg/ml | 26.2 | 7.7 | 51.2 | 31.4 |
| 2.5 µg/ml | 47.7 | 21.8 | 53.6 | 42.1 |
| 5.0 µg/ml | 78.6 | 30.0 | 76.8 | 45.9 |
| 10.0 µg/ml | 83.4 | 51.9 | 85.0 | 47.3 |
| 20.0 µg/ml | 95.5 | 72.1 | 90.2 | 62.0 |
| 40.0 µg/ml | 98.2 | 77.3 | 100.0 | 82.4 |
| *80.0 µg/ml | 100.0 | 88.4 | 100.0 | 94.5 |

*The concentration of 80.0 µg/ml is equal to 148.5 µM

The same type of test was conducted to examine the effect of $M_s32$ against the same four strains of HIV-1. The percentage of HIV-1 inhibition achieved by the different concentrations of $M_s32$ are shown in Table 5 below. The $IC_{50}$ of $M_s32$ for HIV-$1_{RTMF}$, HTLV-$III_{MN}$, HIV-1 $III_BA17$ and HTLV-$III_B$ were 5.6 µg/ml, 5.5 µg/ml, 5.0 µg/ml, and 11 µg/ml, respectively.

TABLE 5

Inhibition of Four Strains HIV-1 Replication by $M_s32$ Drug

| | % Inhibition | | | |
|---|---|---|---|---|
| | HIV-$1_{RTMF}$ | HTLV-$III_{MN}$ | HIV-$III_BA17$ VARIANT | HTLV-$III_B$ |
| 00. µg/ml | 0.0 | 0.0 | 0.0 | 0.0 |
| 1.25 µg/ml | 20.8 | 8.3 | 2.0 | 4.7 |
| 2.5 µg/ml | 38.7 | 45.7 | 21.8 | 16.1 |
| 5.0 µg/ml | 44.2 | 47.0 | 50.0 | 20.1 |
| 10.0 µg/ml | 73.6 | 57.2 | 53.6 | 34.5 |
| 20.0 µg/ml | 90.4 | 87.0 | 97.5 | 90.8 |
| 40.0 µg/ml | 95.0 | 90.0 | 97.7 | 96.2 |
| *80.0 µg/ml | 98.3 | 94.1 | 98.4 | 96.8 |

*The concentration of 80.0 µg/ml is equal to 111.5 µM

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating a retrovirus in a population of cells infected with said retrovirus by reducing or inhibiting the activity of a retroviral integrase, comprising administering to the population of cells a therapeutically effective amount of a purified compound of Formula (1):

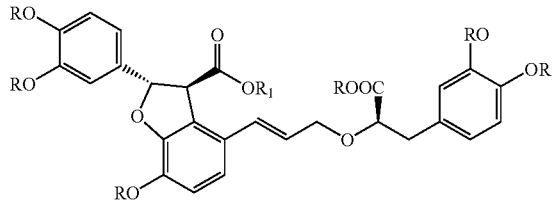

wherein each R is independently H or an alkyl group and $R_1$ is H, alkyl, substituted alkyl, aryl or substituted aryl, or a pharmaceutically acceptable salt thereof, wherein said purified compound is administered in an amount sufficient to reduce the activity of said viral integrase, and wherein the population of cells are cultured in vitro.

2. The method of claim 1, wherein each R and $R_1$ are H.

3. The method of claim 1, wherein $R_1$ is substituted alkyl.

4. The method of claim 1, wherein $R_1$ is:

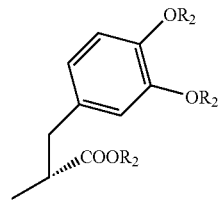

wherein each $R_2$ is independently H or alkyl.

5. The method of claim 4, wherein each $R_2$ is H.

6. The method of claim 1, wherein the virus is a retrovirus.

7. The method of claim 1, wherein the virus is HIV-1.

8. The method of claim 7, wherein the strain of the HIV-1 virus is selected from the group consisting of HIV-$1_{RTMF}$, HIV-$1III_BA17$ variant, HTLV-$III_{MN}$, HTLV-$III_B$, and HIV-$1_{LIOR/M461/L63P/V82T/184V}$.

9. The method of claim 1, wherein the purified compound is administered at a concentration of at least about 0.1 μg/ml.

10. The method of claim 1, wherein the purified compound is administered in a pharmaceutically acceptable carrier.

11. The method of claim 1, wherein the purified compound is administered in combination with at least one additional antiviral agent.

* * * * *

UNITED STATES PATENT AND TRADEMARK OFFICE
CERTIFICATE OF CORRECTION

| | | |
|---|---|---|
| PATENT NO. | : 7,071,227 B2 | Page 1 of 1 |
| APPLICATION NO. | : 09/962923 | |
| DATED | : July 4, 2006 | |
| INVENTOR(S) | : Ru Chih C. Huang, Ibrahim Shawky Abd-Elazem and Hong Shan Chen | |

It is certified that error appears in the above-identified patent and that said Letters Patent is hereby corrected as shown below:

On the title page of the patent, on line 2 of item [75] where the inventors are listed, "Ibrahim Shawky Abd Elazem" should be replaced by --Ibrahim Shawky Abd-Elazem--

Signed and Sealed this

First Day of May, 2007

JON W. DUDAS
*Director of the United States Patent and Trademark Office*